(12) United States Patent
Shuber et al.

(10) Patent No.: US 10,081,829 B1
(45) Date of Patent: Sep. 25, 2018

(54) DETECTION OF TARGETED SEQUENCE REGIONS

(71) Applicant: GENETICS RESEARCH, LLC, Wakefield, MA (US)

(72) Inventors: Anthony P. Shuber, Wakefield, MA (US); William Glover, Wakefield, MA (US); Thomas C. Meyers, Boston, MA (US)

(73) Assignee: GENETICS RESEARCH, LLC, Wakefield, MA (US)

( * ) Notice: Subject to any disclaimer, the term of this patent is extended or adjusted under 35 U.S.C. 154(b) by 0 days.

(21) Appl. No.: 15/877,620

(22) Filed: Jan. 23, 2018

Related U.S. Application Data

(60) Provisional application No. 62/568,144, filed on Oct. 4, 2017, provisional application No. 62/526,091, filed on Jun. 28, 2017, provisional application No. 62/519,051, filed on Jun. 13, 2017.

(51) Int. Cl.
*C12Q 1/68* (2018.01)
*C12Q 1/6806* (2018.01)
*C12Q 1/70* (2006.01)

(52) U.S. Cl.
CPC .......... *C12Q 1/6806* (2013.01); *C12Q 1/701* (2013.01)

(58) Field of Classification Search
None
See application file for complete search history.

(56) References Cited

U.S. PATENT DOCUMENTS

2016/0319262 A1* 11/2016 Doudna ................ C12N 9/22

OTHER PUBLICATIONS

Altmuller, 2014, Enrichment of target sequence for next-generation sequencing applications in research and diagnostics, Biol Chem 395(2)231-37.
Deleavey, 2012, Designing chemically modified oligonucleotides for targeted gene silencing, Chem Biol 19(8):937-54.
Harrington, 2017, A thermostable Cas9 with increased lifetime in human plasma, Nat Commun 8(1):1424.
Jiang, 2015, Cas9-assisted targeting of chromosome segments catch enables one-step targeted cloning of large gene clusters.
Jinek, 2012, A programmable dual-RNA-guided DNA endonuclease in adaptive bacterial immunity, Science 337 (6096):816-821.
Kozarewa, 2015, Overview of Target Enrichment Strategies, Curr Protoc Mol Biol 112(7):1-23.
Mertes, 2011, Targeted enrichment of genomic DNA regions for next-generation sequencing, Brief Fund Genomics 10 (6):374-86.
Monia, 1996, Nuclease resistance and antisense activity of modified oligonucleotides targeted to Ha-ras, J Biol Chem 271(24):14533-40.
Zetsche, 2015, Cpf1 is a single RNA-guided endonuclease of a class 2 CRISPR-Cas system, Cell 163(2):759-71.
Zischewski, 2017, Detection of on-target and off-target mutations generated by CRISPR/Cas9 and other sequence-specific nucleases, Biotechnology Advances 65:95-104.

* cited by examiner

*Primary Examiner* — James S Ketter
(74) *Attorney, Agent, or Firm* — Brown Rudnick LLP; Thomas C. Meyers

(57) ABSTRACT

Provided herein are methods of detecting nucleic acids. The nucleic acid of interest may be detected by using Cas endonuclease to degrade substantially all nucleic acid in a sample except for the nucleic acid of interest, leaving the nucleic acid of interest isolated and amenable to detection. In related methods, Cas endonuclease complexes are used to protect the nucleic acid of interest while unprotected nucleic acid is digested, e.g., by exonuclease, after which the isolated nucleic acid of interest is detected.

19 Claims, 5 Drawing Sheets

DETECTION OF TARGETED SEQUENCE REGIONS

CROSS-REFERENCE TO RELATED APPLICATIONS

This application claims the benefit of, and priority to, U.S. Provisional Application No. 62/568,144, filed Oct. 4, 2017, U.S. Provisional Application No. 62/526,091, filed Jun. 28, 2017, and U.S. Provisional Application No. 62/519,051, filed Jun. 13, 2017, the contents of each of which are incorporated by reference.

TECHNICAL FIELD

The invention generally relates to detection of nucleic acids.

BACKGROUND

Infectious diseases kill many people worldwide each year. One reason that infectious diseases claim so many lives is that pathogens are all around us. We can be infected by harmful microorganisms, such as bacteria, viruses, and fungi, in myriad ways. For example, we ingest them from food and water sources, touch and breathe them in physical environments, including homes, workplaces, places of commerce, and recreational settings, and get exposed to them through contact with other infected individuals.

Unfortunately, detecting a pathogen is difficult because the relevant sample typically includes a large amount of irrelevant material, such as nucleic acids from the host or patient. Irrelevant material interferes with the ability to do PCR or probe hybridization, sometime making detection impossible. Moreover, existing detection methods are limited in the ability to detect large DNA fragments. PCR can introduce errors and fails to capture information about epigenetic modifications such as methylation and may introduce errors in the sequence. In addition, both capture- and amplification-based methods lack the sensitivity to detect targets when the ratio of target-to-background is very low. Finally, the ability to multiplex is limited, making it difficult to detect more than one pathogen in a sample.

SUMMARY

The invention provides methods of detecting a nucleic acid among a population of nucleic acids by selectively degrading all of the nucleic acids other than the one of interest, leaving the nucleic acid of interest isolated and amenable to detection. The methods may be used to detect nucleic acid from a pathogen, to characterize a microbiome of an organism, or to perform metagenomic detection of species in a sample. The detection involves a negative enrichment in which the nucleic acid of interest is isolated by virtue of promiscuous degradation of everything but the nucleic acid of interest. Selective degradation may be accomplished by protecting the ends of the nucleic acid of interest using binding proteins such as Cas endonuclease complexes while degrading the unprotected nucleic acids, e.g., with an exonuclease. Because exonuclease digests everything but the nucleic acid of interest, the described methods effectively isolate the nucleic acid of interest. Because the nucleic acid of interest has been isolated and all other nucleic acid has been degraded, simply detecting the presence of that nucleic acid confirms the presence of, for example, the relevant microbe or pathogen in a subject or sample. Thus, the invention provides methods for rapidly and simply detecting a pathogen in a complex sample, regardless of the presence of nucleic acids from other sources.

Because the methods of the invention provide a simple way to isolate target nucleic acids from a population, they have several advantages over previous methods of target identification. First, the methods are not constrained by the size of the target and thus are able to detect nucleic acids of 10 kb or more. In addition, because irrelevant nucleic acids are degraded, the methods are highly sensitive, allowing detection of targets that are present in the population at very low abundance. The methods do not require copying of the target nucleic acid, obviating concerns over whether a chemical property of the target has been lost or altered during detection. Moreover, the methods can easily be adapted to detect dozens or even hundreds of targets simultaneously in a single assay.

The features described above make the methods of the invention useful for detecting microbes, such as pathogenic organisms, in samples from a variety of sources. For example, the methods can be used to detect viral, bacterial, or fungal infections is tissue from a patient or non-human animal. Other applications include detection of microbes in food, environmental water sources, soil, or agricultural materials. Multiplexing versions of the methods allow identification of the microbiome of a bodily tissue or external sample.

The methods are also useful for detecting endogenous nucleic acids in a sample. For example, the methods permit detection of mitochondrial DNA from samples in which nuclear DNA predominates. Alternatively, mutations in chromosomal DNA can be identified.

The methods are also useful for detecting nucleic acid from an infectious agent, such as a virus, as may present in a host. Methods are addressed to challenges by which viral nucleic acid may be difficult to detect among abundant host DNA.

In an aspect, the invention provides methods of detecting a nucleic acid. The methods include protecting a target nucleic acid in a sample and degrading unprotected nucleic acids. Protection can be mediated by Cas endonuclease complexes. Finally, the methods include detecting the protected nucleic acids. Preferably, the Cas complexes are Cas9 complexes. The Cas complexes that protect the ends of the target nucleic acid may be different from each other, or they may be the same. Preferably, all or nearly all of the unprotected nucleic acids are degraded. Preferably, the protected nucleic acids include the target nucleic acid.

The population of nucleic acids may come from any source. For example, the source may be an organism, such as a human, non-human animal, plant, or other type of organism. The source may be a tissue sample from an animal, such as blood, serum, plasma, skin, conjunctiva, gastrointestinal tract, respiratory tract, vagina, placenta, uterus, oral cavity or nasal cavity. The source may be an environmental source, such as a soil sample or water sample, or a food source, such as a food sample or beverage sample. The nucleic acids may be isolated, purified, or partially purified from a source. Alternatively, nucleic acids may be contained in sample that has not been processed.

The target nucleic acid may be from the genome of a pathogen, such as a virus, bacterium, or fungus. The nucleic acids may come from an organism, and the target nucleic acid may be foreign to the genome of the organism. For example, the target nucleic acid may be from a pathogen of the organism. The target nucleic acid may be from a virus that infects the organism from which the nucleic acids are obtained. The target may be a viral nucleic acid that has integrated into the genome of the host organism. Additionally or alternatively, the target may be a viral nucleic acid that exists separately from the nucleic acids of the host organism. The nucleic acids may come from an organism, and the target nucleic acid may be native to the organism. For example, the target nucleic acid may be from the nuclear genome, mitochondrial genome, or chloroplast genome of the organism.

The target nucleic acid may have a particular size. For example, the nucleic acid of interest may be between 100 and 10,000 nucleotides in length, or it may be greater than 10,000 nucleotides. The nucleic acid of interest may be larger than any remaining nucleic acids after degradation. Thus, the difference in size between the nucleic acid of interest and the nucleic acid fragments after digestion may facilitate detection of the nucleic acid of interest.

The Cas complexes include a Cas endonuclease and a guide RNA. The Cas endonuclease may include any Cas endonuclease. For example, the Cas endonuclease may be Cas9, Cpf1, C2c1, C2c3, C2c2, CasX, or CasY, including modified versions of Cas9, Cpf1, C2c1, C2c3, C2c2, CasX, or CasY in which the amino acid sequence has been altered. The Cas endonuclease is catalytically inactive. For example, the Cas endonuclease may be *Streptococcus pyogenes* Cas9 that has a D10A and/or a R1335K mutation, *Acidaminococcus* sp. BV3L6 Cpf1 that has a D908 mutation, or Lachnospiraceae bacterium ND2006 that has a D832 mutation.

The guide RNAs may be any guide RNA that functions with a Cas endonuclease. Individual guide RNAs may include a separate crRNA molecule and tracrRNA molecule, or individual guide RNAs may be single molecules that include both crRNA and tracrRNA sequences.

Protection of the ends of the target nucleic acid may include the binding of the Cas complexes to one or both ends. The Cas complexes that bind to the ends of the target nucleic acid may be catalytically inactive. Protection of the ends of the target nucleic acid may include cleavage of the target nucleic acids at one or both ends.

Degradation of unprotected nucleic acids may include digestion with an exonuclease, such as exonuclease I, exonuclease II, exonuclease III, exonuclease IV, exonuclease V, exonuclease VI, exonuclease VII, or exonuclease VIII.

The target nucleic acid may be detected by any suitable means, such as by hybridization, spectrophotometry, sequencing, electrophoresis, amplification, fluorescence detection, or chromatography.

In another aspect, the invention provides methods of detecting a microbe in which the methods include the following steps: protecting the ends of a target nucleic acid from a genome of a microbe in a sample using a pair of Cas complexes; degrading unprotected nucleic acids; and detecting the protected nucleic acid, which indicates the presence of the microbe in the sample. Preferably, the Cas complexes are Cas9 complexes. The Cas complexes in a pair may be different from each other, or they may be the same. Preferably, all or nearly all of the unprotected nucleic acids are degraded. Preferably, the protected nucleic acids include the target nucleic acid.

The methods may include detecting multiple microbes in a sample. For example, the methods may include determining the microbiome of a sample. In such methods, multiple target nucleic acids are detected using multiple pairs of Cas complexes. For example, the methods may include sets of Cas complexes that include at least 1000 pairs. When multiple microbes are detected in a sample, the methods may include determining the relative abundance of different microbes in the sample. The methods may include counting the different target nucleic acids to determine the relative abundance of microbes in the sample. One or more of the microbes in the sample may be pathogens, such as a viruses, bacteria, or fungi.

The sample may come from any source. For example, the source may be an organism, such as a human, non-human animal, plant, or other type of organism. The source may be a tissue sample from an animal, such as blood, serum, plasma, skin, conjunctiva, gastrointestinal tract, respiratory tract, vagina, placenta, uterus, oral cavity or nasal cavity. The source may be an environmental source, such as a soil sample or water sample, or a food source, such as a food sample or beverage sample. The sample may comprise nucleic acids that have been isolated, purified, or partially purified from a source. Alternatively, the sample may not have been processed.

The target nucleic acids may have a particular size. For example, the target nucleic acids may be between 100 and 10,000 nucleotides in length, or it may be greater than 10,000 nucleotides in length.

The Cas complexes include a Cas endonuclease and a guide RNA. The Cas endonuclease may include any Cas endonuclease. For example, the Cas endonuclease may be Cas9, Cpf1, C2c1, C2c3, C2c2, CasX, or CasY, including modified versions of Cas9, Cpf1, C2c1, C2c3, C2c2, CasX, or CasY in which the amino acid sequence has been altered. The Cas endonuclease is catalytically inactive. For example, the Cas endonuclease may be *Streptococcus pyogenes* Cas9 that has a D10A and/or a R1335K mutation, *Acidaminococcus* sp. BV3L6 Cpf1 that has a D908 mutation, or Lachnospiraceae bacterium ND2006 that has a D832 mutation.

The guide RNAs may be any guide RNA that functions with a Cas endonuclease. Individual guide RNAs may include a separate crRNA molecule and tracrRNA molecule, or individual guide RNAs may be single molecules that include both crRNA and tracrRNA sequences.

The set of Cas complexes may include a single Cas endonuclease and multiple pairs of guide RNAs.

Protection of the ends of the target nucleic acid may include the binding of the Cas complexes to one or both ends. The Cas complexes that bind to the ends of the target nucleic acid may be catalytically inactive.

Protection of the ends of the target nucleic acid may include cleavage of the target nucleic acids at one or both ends.

Degradation of unprotected nucleic acids may include digestion with an exonuclease, such as exonuclease I, exonuclease II, exonuclease III, exonuclease IV, exonuclease V, exonuclease VI, exonuclease VII, or exonuclease VIII.

The target nucleic acid may be detected by any suitable means, such as by hybridization, spectrophotometry, sequencing, electrophoresis, amplification, fluorescence detection, or chromatography.

In another aspect, the invention provides methods of detecting a nucleic acid. The methods include exposing a population of nucleic acids containing a nucleic acid of interest to a set of complexes, each of which contains a Cas endonuclease and a guide RNA that targets a sequence absent from the nucleic acid of interest; digesting the targeted nucleic acids using the Cas endonuclease-guide RNA complexes; and detecting the nucleic acid of interest. The population of nucleic acids may come from any source. For example, the source may be an organism, such as a human, non-human animal, plant, or other type of organism. The source may be a tissue sample from an animal, such as blood, serum, plasma, skin, conjunctiva, gastrointestinal tract, respiratory tract, vagina, placenta, uterus, oral cavity or nasal cavity. The source may be an environmental source, such as a soil sample or water sample, or a food source, such as a food sample or beverage sample. The nucleic acids may be isolated, purified, or partially purified from a source. Alternatively, nucleic acids may be contained in sample that has not been processed.

The nucleic acid of interest may be from the genome of a pathogen, such as a virus, bacterium, or fungus. The nucleic acids may come from an organism, and the nucleic acid of interest may be foreign to the genome of the organism. For example, the nucleic acid of interest may be from a pathogen of the organism. The nucleic acid of interest may be from a virus that infects the organism from which the nucleic acids are obtained. The nucleic acid of interest may be a viral nucleic acid that has integrated into the genome of the host organism. Additionally or alternatively, the nucleic acid of interest may be a viral nucleic acid that exists separately from the nucleic acids of the host organism. The nucleic acids may come from an organism, and the nucleic acid of interest may be native to the organism. For example, the nucleic acid of interest may be from the nuclear genome, mitochondrial genome, or chloroplast genome of the organism.

The nucleic acid of interest may have a particular size. For example, the nucleic acid of interest may be between 100 and 10,000 nucleotides in length, or it may be greater than 10,000 nucleotides. The nucleic acid of interest may be larger than any remaining nucleic acids after digestion. Thus, the difference in size between the nucleic acid of interest and the nucleic acid fragments after digestion may facilitate detection of the nucleic acid of interest.

The complexes may include any Cas endonuclease. For example, the Cas endonuclease may be Cas9, Cpf1, C2c1, C2c3, C2c2, CasX, or CasY, including modified versions of Cas9, Cpf1, C2c1, C2c3, C2c2, CasX, or CasY in which the amino acid sequence has been altered.

The guide RNAs may be any guide RNA that functions with a Cas endonuclease. Individual guide RNAs may include a separate crRNA molecule and tracrRNA molecule, or individual guide RNAs may be single molecules that include both crRNA and tracrRNA sequences.

The set of complexes may include a single Cas endonuclease and a set of guide RNAs. The set may include at least 1000 different complexes.

Digestion of the targeted nucleic acids may cleave the targeted nucleic acids to molecules of a certain size. For example, the digested nucleic acids may be less than about 5000 nucleotides. Digested nucleic acids may be smaller than the nucleic acid of interest, thereby facilitating detection of the nucleic acid of interest.

The nucleic acid of interest may be detected by any suitable means, such as by hybridization, spectrophotometry, sequencing, electrophoresis, amplification, fluorescence detection, or chromatography.

DETAILED DESCRIPTION

Provided herein are methods of detecting nucleic acids. The nucleic acid of interest may be detected by first using Cas endonuclease to degrade substantially all nucleic acid in a sample except for the nucleic acid of interest, then detected the presence of the nucleic acid of interest. In related methods, Cas endonuclease complexes are used to protect the nucleic acid of interest while unprotected nucleic acid is digested, e.g., by exonuclease, followed by detecting the nucleic acid of interest that remains. The invention provides methods of detecting a nucleic acid of interest in a population of nucleic acids by eliminating all of the nucleic acids other than the one of interest. Because the methods of the invention do not require "fishing" target nucleic acids from a population, they avoid problems of target size, sensitivity, and target adulteration associated with methods that rely on hybrid capture or PCR amplification. In addition, the methods of the invention allow detection of multiple nucleic acids of interest in a single assay.

The aforementioned advantages make the methods of the invention useful for a variety of applications. For example, the methods can be used to detect foreign nucleic acids in a host organism. Thus, they allow detection of infectious agents, such as viruses, bacteria, and fungi, in humans, other animals, and plants. In particular, pathogenic microbes can be detected. Alternatively, they permit detection of low-abundance nucleic acids that are native to an organism, such as genes from a mitochondrial or chloroplast genome or nuclear genes that are present in only a minority of cells in a sample. The methods can also be used to detect nucleic acids from a microbe, and thus the microbe itself, in a sample from an environmental source, such as a soil or water, or from a food source. In addition, because multiple nucleic acids can be simultaneously detected, the methods of the invention are useful for determining the microbiome of a sample, such as bodily tissue or an external source.

Figure 1:
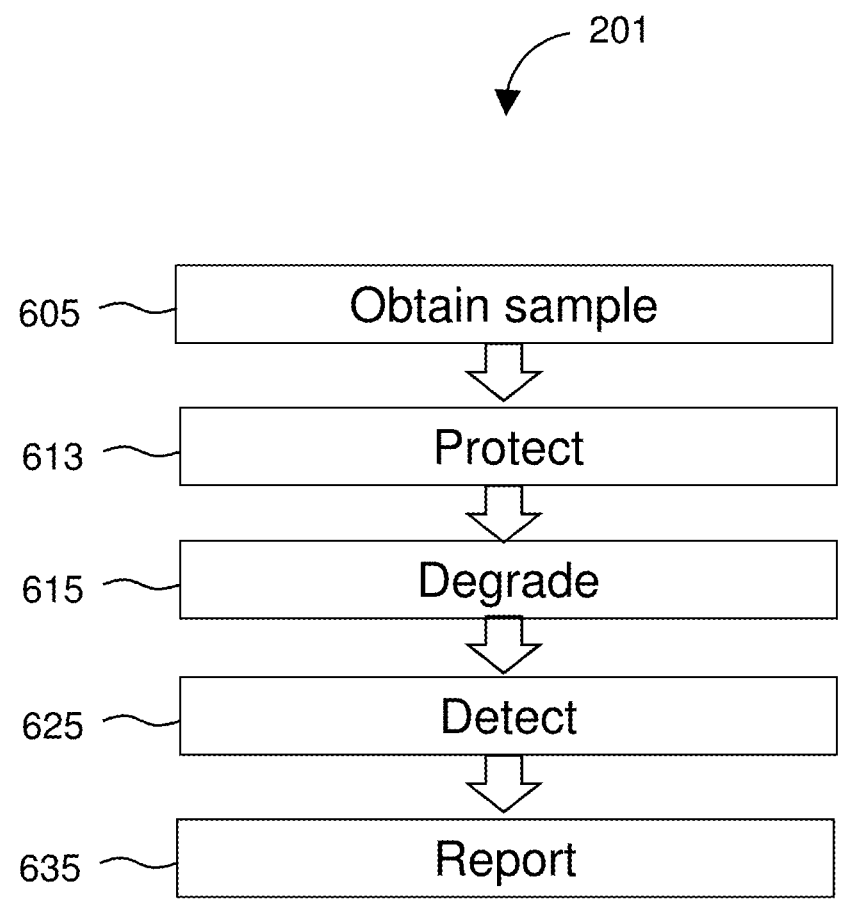
FIG. 1 diagrams a method of detecting a nucleic acid in a second embodiment.

FIG. 1 diagrams a method 201 of detecting a nucleic acid. The method 201 includes obtaining 605 a sample. The method includes protecting 613, in a population of nucleic acids, first and/or second ends of a target nucleic acid using respective first and/or second binding proteins such as Cas endonuclease (e.g., complexed with a guide RNA). The method 201 further includes degrading 615 unprotected nucleic acids and detecting 625 the protected nucleic acid. Preferably, the detected nucleic acid is reported 635 as being present in the sample.

Figure 2:
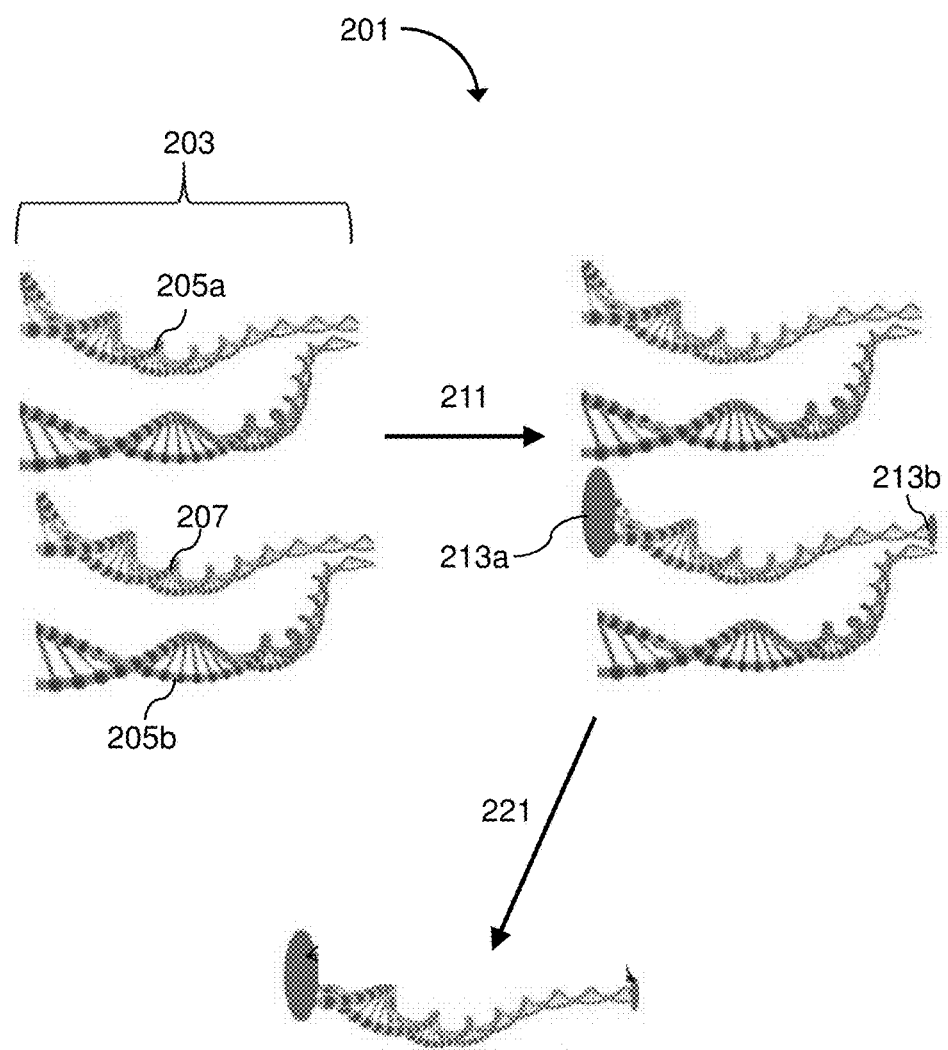
FIG. 2 illustrates the second embodiment of the invention.

FIG. 2 illustrates the method 201. A population 203 of nucleic acids 205a, 205b, including a target nucleic acid 207, is provided. The target nucleic acid 207 is protected 211 by allowing Cas complexes 213a, 213b to bind to sequences at the ends of the target nucleic acid 207. The target nucleic acid 207 may be a portion of larger nucleic acid molecule, and the ends of the target nucleic acid 207 may not be the ends of a nucleic acid molecule, i.e., the ends may not be free 5' phosphate groups or free 3' OH groups. Binding of the Cas complexes to the ends of the target nucleic provides protection against exonuclease digestion. Nucleic acids 205a, 205b in the population 203 are then degraded 221, but the target nucleic acid 207 is protected from degradation. Preferably, degradation occurs via exonuclease digestion. The target nucleic acid 207 may then be detected by any suitable means.

The nucleic acids may come from any source, as described elsewhere herein. Also, as described elsewhere herein, the nucleic acids may have been isolated, purified, or partially purified, or the samples may not have been processed. The target nucleic acid may be any nucleic acid of interest of any size, as described elsewhere herein.

The methods are also useful for detecting nucleic acid from an infectious agent, such as a virus, as may present in a host. Methods are addressed to challenges by which viral nucleic acid may be difficult to detect among abundant host DNA. Thus the detected nucleic acid may be of an infecting virus. Obtaining the sample may include taking a tissue sample from a patient and extracting or accessing DNA therein. The DNA of an infecting virus is isolated by digesting away substantial amounts of non-viral DNA. E.g., using method 101, a plurality of guide RNAs specific to a human genome (but having no match in the viral genome) is used to digest away the host genetic material, leaving only viral DNA present, such that detecting the viral DNA confirms the presence of the virus in the patient. Preferably, method 201 is used and the viral DNA is protected using binding proteins (e.g., Cas endonuclease) while unprotected nucleic acid is ablated (using, e.g., exonuclease). The detected viral DNA may be of any suitable virus including retroviruses that integrate into the host genome and virus present as viral episomes.

Thus in a preferred embodiment, the method includes providing guide RNAs that are specific to a viral genome, such as HIV, and using those guide RNAs with Cas endonuclease to protect a fragment of viral DNA in a sample from a patient. After digesting away unprotected DNA, the remaining DNA is detected, confirming the presence of the virus in the host genome. The methods thus provides a rapid and reliable viral test, that can detect retroviral proviral DNA and/or viral episomes, and thus detect viral infections at any stage.

The Cas complexes may include any Cas endonuclease, as described elsewhere herein. The Cas endonuclease may be catalytically inactive. For example and without limitation, the Cas endonuclease may be *Streptococcus pyogenes* Cas9 that has a D10A and/or R1335K mutation, *Acidaminococcus* sp. BV3L6 Cpf1 that has a D908 mutation, or Lachnospiraceae bacterium ND2006 that has a D832 mutation.

The Cas complexes that bind the ends of the target nucleic acid may be different from each other, or they may be the same. Preferably, the Cas complexes that bind the ends of the target nucleic acid have the same Cas endonuclease complexed with different guide RNAs, with each guide containing a sequence that targets one end of the target nucleic acid.

The guide RNAs may be single-molecule guides or two-molecule guides, as described elsewhere herein.

Degradation of unprotected nucleic acids may occur by any suitable means. Preferably, unprotected nucleic acids are degraded by digestion with an exonuclease, such as exonuclease I, exonuclease II, exonuclease III, exonuclease IV, exonuclease V, exonuclease VI, exonuclease VII, or exonuclease VIII. Digestion may destroy all or substantially all nucleic acids in the population other than the target. For example, at least 90%, at least 95%, at least 98%, at least 99%, at least 99.9% of targeted nucleic acids may be digested. Digestion may degrade nucleic acids to individual nucleotides or to small fragments that are distinguishable from the intact target. For example, after degradation, nucleic acids other than the target may have fewer than 20 nucleotides, fewer than 10 nucleotides, fewer than 5 nucleotides, fewer than 4 nucleotides, or fewer than 3 nucleotides.

After digestion, the target nucleic acid may be detected by any suitable means, as described elsewhere herein.

Protection of the target nucleic acid may occur simply by binding of a Cas complex to each end of the target, thereby preventing exonuclease digestion of the target. Alternatively or additionally, protection may involve binding of the Cas complexes or cleavage of at one or both of the binding sites near the end of the target nucleic acid.

In certain embodiments, the method 201 has applications in metagenomics. Metagenomics includes to the study of genetic material recovered directly from environmental samples. While traditional microbiology and microbial genome sequencing and genomics relied upon cultivated clonal cultures, early environmental gene sequencing cloned specific genes (often the 16S rRNA gene) to produce a profile of diversity in a natural sample. Here, methods of the invention are useful to take essentially unbiased samples of all genes from all the members of the sampled communities. Because of their ability to reveal the previously hidden diversity of microscopic life, methods of the disclosure applied to metagenomics offers novel views of the microbial world. Specifically, using a mixture of guide RNAs, method 201 may be used to isolate a plurality of representative sample fragments of microbial DNA from an environmental sample, such that the set of sample fragments are a representative sample of microbial diversity in the environmental sample. In some embodiments, the methods 201 are performed with an abundance of pseudo-random guide RNAs in Cas endonuclease complexes. Pairs of the complexes isolate DNA fragments from an environmental sample. The collected set of fragments is essentially a vertical slice through the microbial genetic information in the sample, and thus is representative of microbial diversity therein. Those fragments may be analyzed to reveal microbial diversity in the sample, even without culturing individual microbes or knowing a priori the species that may be present in the sample. The fragments may be analyze by, for example, sequencing. Since methods of the invention are useful to isolate long, intact nucleic acid molecules, the methods are particularly useful for long-read, single-molecule sequencing platforms such as those of Oxford Nanopore or Pacific Biosciences. Using such a sequencing platform with a method 201, one may perform a metagenomic survey of a sample and microbial ecology may thus be investigated at a much greater scale and detail than before.

Methods of the invention can be used to identify the microbiome, i.e., the collective genetic material of the microbiota. The microbiota is the ecological community of commensal, symbiotic and pathogenic microorganism found in and on all multicellular organisms studied to date. A microbiota includes bacteria, archaea, protists, fungi and viruses. Microbiota have been found to be crucial for immunologic, hormonal, and metabolic homeostasis of their host. The symbiotic relationship between a host and its microbiota shapes the immune system of mammalians, insects, plants, and aquatic organisms.

Embodiments of the invention include identification of a microbiome from a sample. Such embodiments include a method 101 or method 201 of detecting a nucleic acid of interest. The methods may include detecting multiple microbes in a sample. Preferably, methods include protecting one or both ends of a nucleic acid from a genome of a microbe in a sample using a first Cas9 complex and a second Cas9 complex, degrading unprotected nucleic acids, and detecting at least one protected nucleic acid, thereby detecting the microbe in the sample. Multiple nucleic acids from multiple microbes can be detected using sets of pairs of Cas9 complexes, allowing the microbiome of a sample to be determined. The method may include reporting the microbiome of a sample.

Kits and methods of the invention are useful with methods disclosed in U.S. Provisional Patent Application 62/526,091, filed Jun. 28, 2017, for POLYNUCLEIC ACID MOLECULE ENRICHMENT METHODOLOGIES and U.S. Provisional Patent Application 62/519,051, filed Jun. 13, 2017, for POLYNUCLEIC ACID MOLECULE ENRICHMENT METHODOLOGIES, both incorporated by reference.

The method 201 uses a double-protection to select one or both ends of DNA segments. Unprotected segments are digested and the remaining molecules are either counted or sequenced. The method 201 is well suited for the analysis of small portions of DNA, degraded samples, samples in which the target of interest is extremely rare, and particularly for environmental samples, e.g., for pathogen detection or metagenomics.

The method 201 includes a negative enrichment step that leaves the target of interest intact and isolated as a segment of DNA. The methods are useful for the isolation of intact DNA fragments of any arbitrary length and may preferably be used in some embodiments to isolate (or enrich for) arbitrarily long fragments of DNA, e.g., tens, hundreds, thousands, or tens of thousands of bases in length or longer. Long, isolated, intact fragments of DNA may be analyzed by any suitable method such as simple detection (e.g., via staining with ethidium bromide) or by single-molecule sequencing. Embodiments of the invention provide kits that may be used in performing methods described herein.

Figure 3:
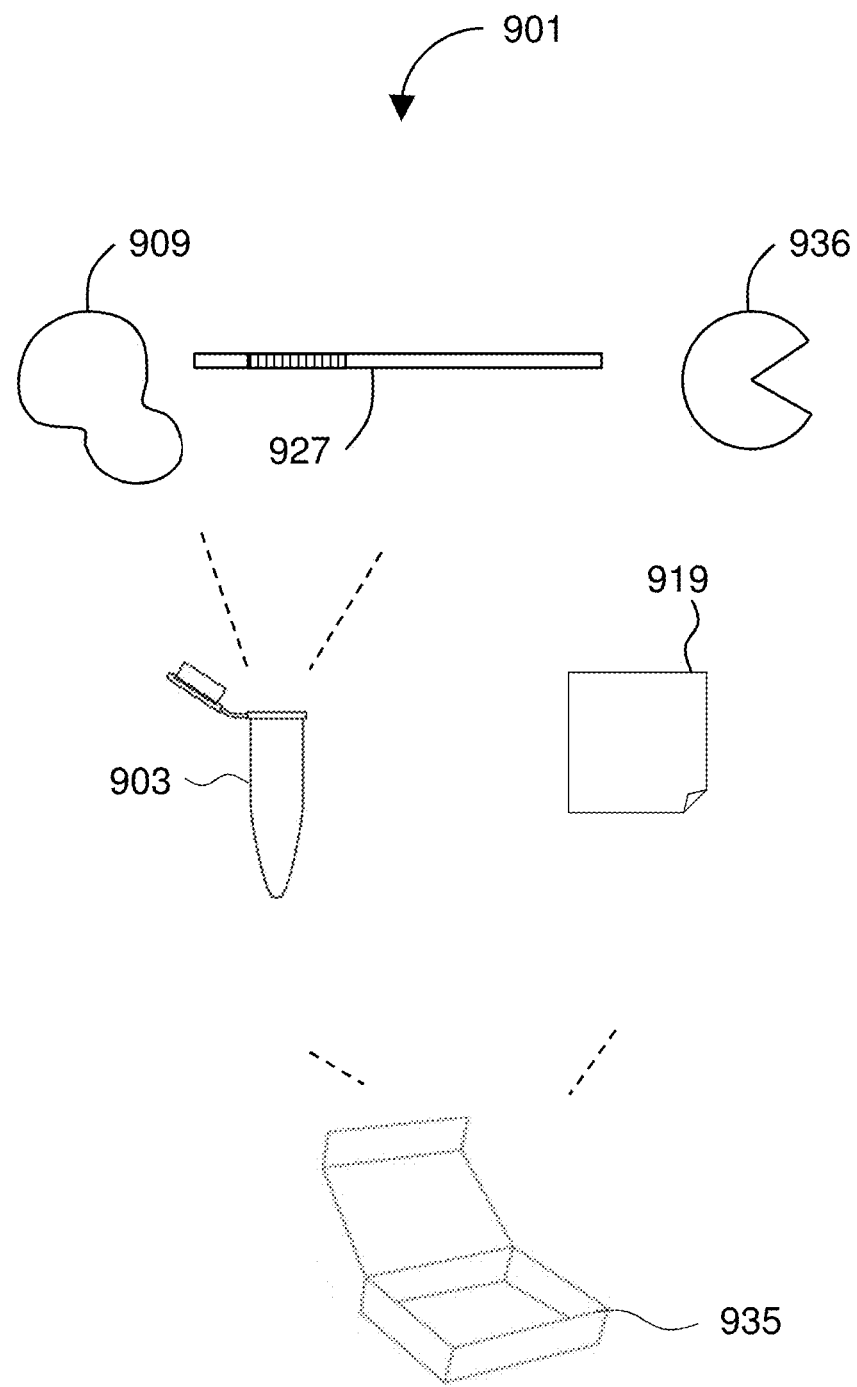
FIG. 3 shows a kit of the invention.

FIG. 3 shows a kit 901 of the invention. The kit 901 may include reagents 903 for performing the steps described herein. For example, the reagents 903 may include one or more of a Cas endonuclease 909, a guide RNA 927, and exonuclease 936. The kit 901 may also include instructions 919 or other materials. The reagents 903, instructions 919, and any other useful materials may be packaged in a suitable container 935. Kits of the invention may be made to order. For example, an investigator may use, e.g., an online tool to design guide RNA and reagents for the performance of methods 101, 201. The guide RNAs 927 may be synthesized using a suitable synthesis instrument. The synthesis instrument may be used to synthesize oligonucleotides such as gRNAs or single-guide RNAs (sgRNAs). Any suitable instrument or chemistry may be used to synthesize a gRNA. In some embodiments, the synthesis instrument is the MerMade 4 DNA/RNA synthesizer from Bioautomation (Irving, Tex.). Such an instrument can synthesize up to 12 different oligonucleotides simultaneously using either 50, 200, or 1,000 nanomole prepacked columns. The synthesis instrument can prepare a large number of guide RNAs 927 per run. These molecules (e.g., oligos) can be made using individual prepacked columns (e.g., arrayed in groups of 96) or well-plates. The resultant reagents 903 (e.g., guide RNAs 917, endonuclease(s) 909, exonucleases 936) can be packaged in a container 935 for shipping as a kit.

Figure 4:
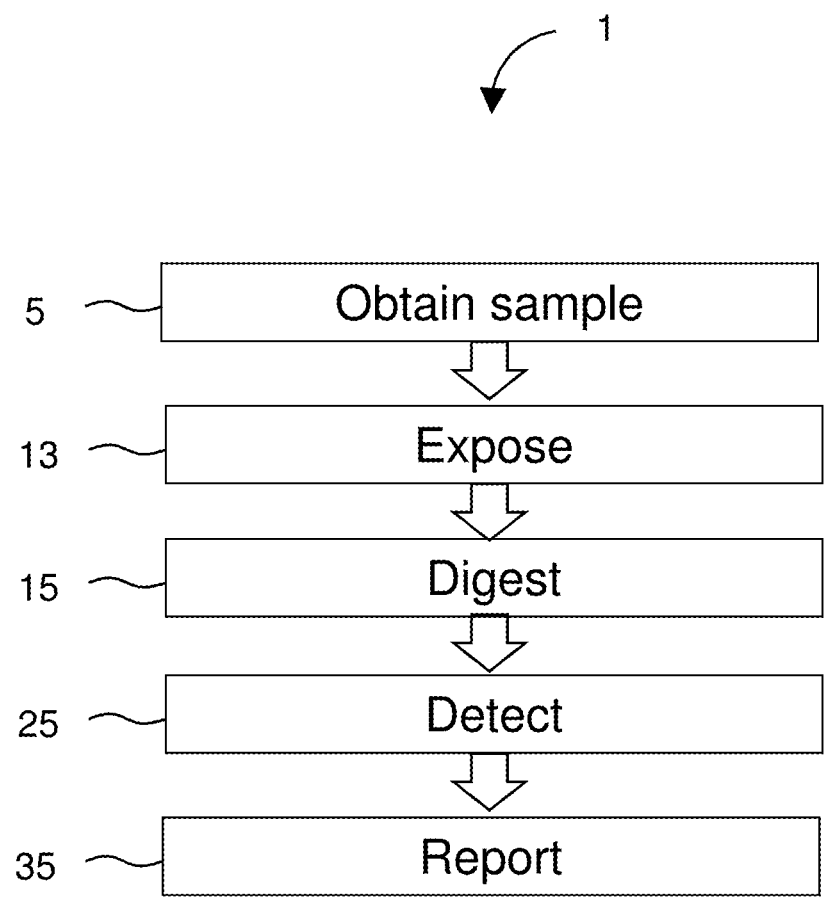
FIG. 4 diagrams a method of detecting a nucleic acid in a first embodiment.

The invention also provides an alternative method of detecting a nucleic acid of interest. FIG. 4 diagrams a method 101 of detecting a nucleic acid. The method 101 includes obtaining 5 a sample and exposing 13 a population of nucleic acids comprising a nucleic acid of interest to a plurality of complexes. Each complex includes a Cas endonuclease and a guide RNA that targets a sequence absent from the nucleic acid of interest. The method 101 includes digesting 15 nucleic acids targeted by the plurality of complexes using the plurality of complexes and detecting 25 the nucleic acid of interest. The method 101 may optionally include reporting 35 the nucleic acid of interest in the sample.

Figure 5:
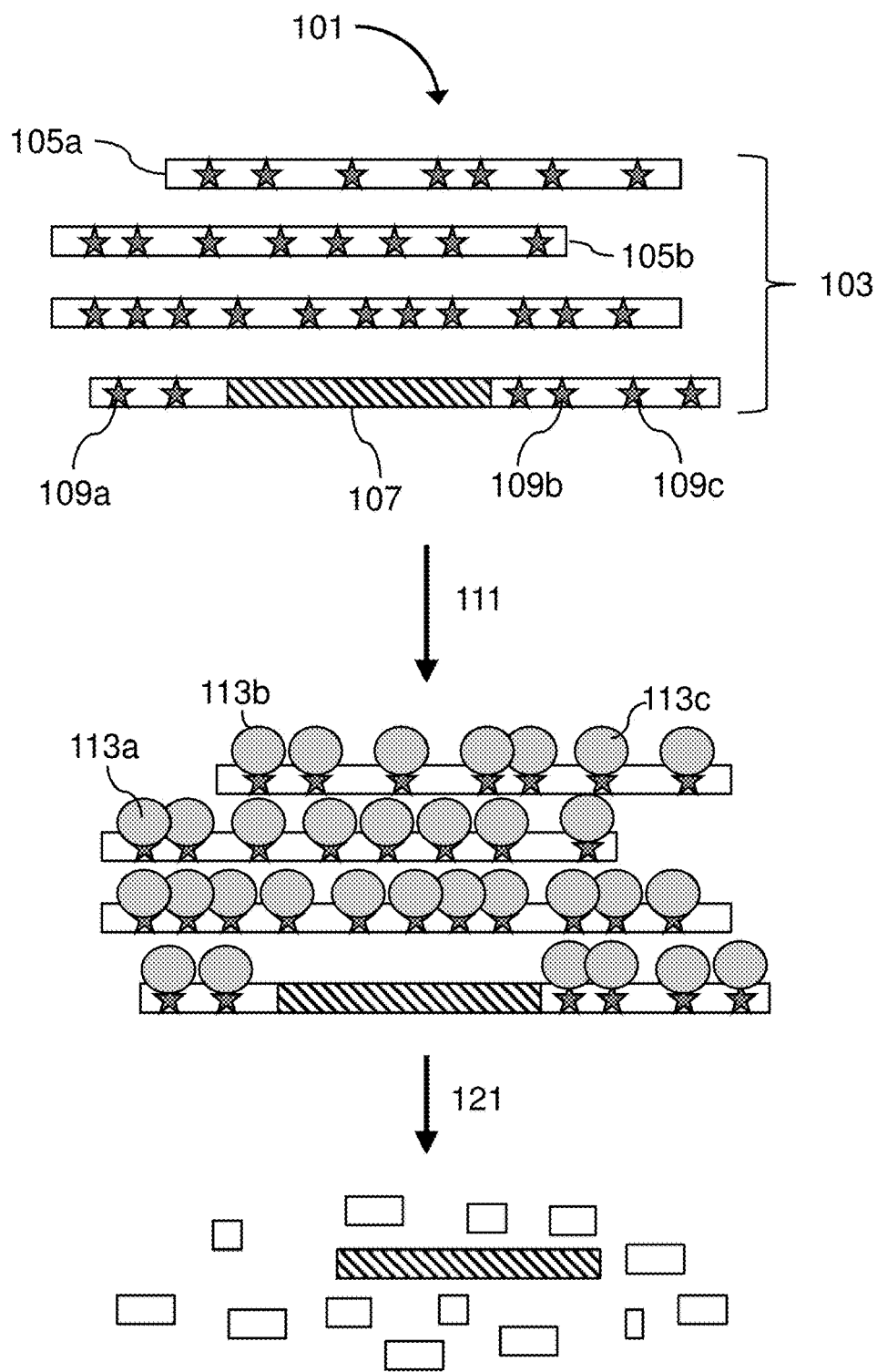
FIG. 5 illustrates a method of detecting a nucleic acid in the first embodiment.

FIG. 5 illustrates the method 101. A population 103 of nucleic acids 105a, 105b, including a nucleic acid of interest 107, is provided. The nucleic acids 105a, 105b include numerous target sequences 109a, 109b, and 109c for a set of Cas complexes 113a, 113b, 113c, but the nucleic acid of interest does not contain a target sequence. The population 103 is exposed 111 to the set of Cas complexes 113a, 113b, and 113c, which are targeted to the various target sequences 109a, 109b, and 109c. The nucleic acids 105a, 105b are then digested 121 by the Cas complexes 113a, 113b, and 113c. Most nucleic acids 105a, 105b are digested into small fragments, but the nucleic acid of interest 107, which was not targeted by a Cas complex, remains intact. The nucleic acid of interest 107 may then be detected by any suitable means.

The Cas complexes include a Cas endonuclease and a guide RNA. For example, the Cas endonuclease may be Cas9, Cpf1, C2c1, C2c3, C2c2, CasX, or CasY, including sequence variants of Cas9, Cpf1, C2c1, C2c3, C2c2, CasX, or CasY. Preferably, the Cas endonuclease is Cas9. The Cas endonuclease may be from any bacterial species. For example and without limitation, the Cas endonuclease may be from *Bacteroides coprophilus, Campylobacter jejuni* susp. *jejuni, Campylobacter lari, Fancisella novicida, Filifactor alocis, Flavobacterium columnare, Fluviicola taffensis, Gluconacetobacter diazotrophicus, Lactobacillus farciminis, Lactobacillus johnsonii* (e), *Legionella pneumophila, Mycoplasma gallisepticum, Mycoplasma mobile, Neisseria cinerea, Neisseria meningitidis, Nitratifractor salsuginis, Parvibaculum lavamentivorans, Pasteurella multocida, Sphaerochaeta globusa, Streptococcus pasteurianus, Streptococcus thermophilus, Sutterella wadsworthensis,* and *Treponema denticola.*

A guide RNA mediates binding of the Cas complex to the guide RNA target site via a sequence complementary to a sequence in the target site. Typically, guide RNAs that exist as single RNA species comprise a CRISPR (cr) domain that is complementary to a target nucleic acid and a tracr domain that binds a CRISPR/Cas protein. However, guide RNAs may contain these domains on separate RNA molecules.

Typically, the set of Cas complexes includes a single Cas endonuclease and a panel of guide RNAs that have common tracr sequences and different targeting sequences. The panel of targeting sequences includes sequences complementary to as many regions in the population of nucleic acids as possible without targeting the nucleic acid of interest. For example, if the population of nucleic acids is from a host organism and the nucleic acid of interest is from a microbial pathogen of that host, the panel of guide RNAs may be designed to target sites throughout the host genome without targeting a sequence from the genome of the microbial pathogen. For example, the panel of guide RNAs may include at least 100, at least 1000, at least 10,000, at least 100,000 at least 1,000,000, or at least 10,000,000 different species. Thus, when the guide RNAs from the panel are complexed with the Cas endonuclease, the set of complexes may include at least 100, at least 1000, at least 10,000, at least 100,000 at least 1,000,000, or at least 10,000,000 different complexes.

The population of nucleic acids may come from any source. The source may be an organism, such as a human, non-human animal, plant, or other type of organism. The source may be a tissue sample from an animal, such as blood, serum, plasma, skin, conjunctiva, gastrointestinal tract, respiratory tract, vagina, placenta, uterus, oral cavity or nasal cavity. The source may be an environmental source, such as a soil sample or water sample, or a food source, such as a food sample or beverage sample.

The population of nucleic acids may have been isolated, purified, or partially purified from a source. Techniques for preparing nucleic acids from tissue samples and other sources are known in the art and described, for example, in Green and Sambrook, Molecular Cloning: A Laboratory Manual (Fourth Edition), Cold Spring Harbor Laboratory Press, Woodbury, N.Y. 2,028 pages (2012), incorporated herein by reference. Alternatively, the nucleic acids may be contained in sample that has not been processed. The nucleic acids may single-stranded or double-stranded. Double-stranded nucleic acids may be DNA, RNA, or DNA/RNA hybrids. Preferably, the nucleic acids are double-stranded DNA.

The nucleic acid of interest may be from the genome of a pathogen, such as a virus, bacterium, or fungus. The population of nucleic acids may come from an organism, and the nucleic acid of interest may be foreign to the genome of the organism. For example, the nucleic acid of interest may be from a pathogen of the organism. The nucleic acid of interest may be from a virus that infects the organism from which the nucleic acids are obtained. The nucleic acid of interest may be a viral nucleic acid that has integrated into the genome of the host organism. Additionally or alternatively, the nucleic acid of interest may be a viral nucleic acid that exists separately from the nucleic acids of the host organism. The nucleic acid of interest may be native to the organism from which the population has been obtained. For example, the nucleic acid of interest may be from the nuclear genome, mitochondrial genome, or chloroplast genome of the organism. The population of nucleic acids may come from a tissue sample from an organism, and the nucleic acid of interest may be a nucleic acid that is present in that tissue in a low abundance and/or is indicative of a pathological or medical condition.

The nucleic acid of interest may have a particular size. For example, the nucleic acid of interest may be between 100 and 10,000 nucleotides in length, or it may be greater than 1000 nucleotides in length.

Digestion of the targeted nucleic acids may cleave the targeted nucleic acids to molecules of a certain size. For example, the digested nucleic acids may be less than about 10 nucleotides, less than about 20 nucleotides, less than about 50 nucleotides, less than about 100 nucleotides, less than about 200 nucleotides, less than about 500 nucleotides, less than about 1000 nucleotides, less than about 2000 nucleotides, or less than about 5000 nucleotides. Digested nucleic acids may be smaller than the nucleic acid of interest. All or substantially all targeted nucleic acids may be digested. For example, at least 90%, at least 95%, at least 98%, at least 99%, at least 99.9% of targeted nucleic acids may be digested.

The nucleic acid of interest may be detected by any suitable means. Methods of detection of nucleic acids are known in the art and described, for example, in Green and Sambrook, Molecular Cloning: A Laboratory Manual (Fourth Edition), Cold Spring Harbor Laboratory Press, Woodbury, N.Y. 2,028 pages (2012), incorporated herein by reference. For example and without limitation, nucleic acid of interest may be detected by hybridization, spectrophotometry, sequencing, electrophoresis, amplification, fluorescence detection, or chromatography. Detection may be based on difference in size between the nucleic acid of interest and the fragments of other nucleic acids that remain after digestion. For example, after digestion, fragments of targeted nucleic acids may fall below a threshold size, while the nucleic acid of interest may exceed the threshold size. For example, after digestion, the nucleic acid of interest may be the only nucleic acid greater than about 10 nucleotides, greater than about 20 nucleotides, greater than about 50 nucleotides, greater than about 100 nucleotides, greater than about 200 nucleotides, greater than about 500 nucleotides, greater than about 1000 nucleotides, greater than about 2000 nucleotides, or greater than about 5000 nucleotides.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of detecting a nucleic acid, the method comprising:
   protecting, in a population of nucleic acids, first and second ends of a target nucleic acid using a first Cas endonuclease and a second Cas endonuclease;
   digesting unprotected nucleic acids with exonuclease; and
   detecting at least one protected nucleic acid.

2. The method of claim 1, wherein:
   the first Cas endonuclease and the second Cas endonuclease complex are different,
   substantially all of the unprotected nucleic acids are digested, and
   the target nucleic acid is from a genome of a pathogen.

3. The method of claim 1, wherein the at least one protected nucleic acid comprises the target.

4. The method of claim 1, wherein the first Cas endonuclease comprises a first Cas9 protein complexed with a first guide RNA, and the second Cas endonuclease comprises a second Cas9 protein complexed with a second guide RNA.

5. The method of claim 4, wherein at least one of the first Cas9 complex and the second Cas9 complex comprises a catalytically inactive Cas9 protein.

6. The method of claim 1, wherein the target nucleic acid is from a genome of a pathogen.

7. The method of claim 1, wherein the population of nucleic acids is isolated from an organism and the target nucleic acid comprises a sequence foreign to a genome of the organism.

8. The method of claim 7, wherein the target nucleic acid is from a genome of a pathogen of the organism.

9. The method of claim 8, wherein the pathogen is a virus, bacterium, or fungus.

10. The method of claim 9, wherein the pathogen is a virus, and the target nucleic acid is integrated into a nucleic acid within the genome of the organism.

11. The method of claim 10, wherein the pathogen is a virus, and the target nucleic acid exists separately from nucleic acids within the genome of the organism.

12. The method of claim 1, wherein: the population of nucleic acids is isolated from an organism and the target nucleic acid is from a mitochondrial genome of the organism.

13. The method of claim 1, wherein the population of nucleic acids is isolated from a source selected from the group consisting of a soil sample, a water sample, and a food sample.

14. The method of claim 13, wherein the target nucleic acid is from a genome of a pathogen.

15. The method of claim 1, wherein:
the population of nucleic acids is from a sample, and
a plurality of nucleic acids from genomes of organisms in the sample are detected, thereby identifying the metagenome of the sample.

16. The method of claim 1, wherein:
the population of nucleic acids is from a sample, and
a plurality of nucleic acids from genomes of microbes are detected, thereby identifying the microbiome of the sample.

17. The method of claim 1, wherein the detecting step comprises one selected from the group consisting of hybridization, spectrophotometry, sequencing, electrophoresis, amplification, fluorescence detection, and chromatography.

18. The method of claim 1, wherein the detecting step comprises sequencing.

19. A method of detecting a microbe, the method comprising:
protecting first and second ends of a nucleic acid from a genome of a microbe in a sample using a first Cas9 complex and a second Cas9 complex;
digesting unprotected nucleic acids with exonuclease; and
detecting the protected nucleic acid, thereby detecting the microbe in the sample.

* * * * *